United States Patent
Davi

(10) Patent No.: US 10,406,338 B2
(45) Date of Patent: Sep. 10, 2019

(54) TRANSDERMAL STIMULATOR AND MEDICANT MEDICAL DELIVERY DEVICE

(71) Applicant: Richard A. Davi, Glenwood, NJ (US)

(72) Inventor: Richard A. Davi, Glenwood, NJ (US)

(*) Notice: Subject to any disclaimer, the term of this patent is extended or adjusted under 35 U.S.C. 154(b) by 514 days.

(21) Appl. No.: 15/183,345

(22) Filed: Jun. 15, 2016

(65) Prior Publication Data

US 2016/0367773 A1    Dec. 22, 2016

Related U.S. Application Data

(60) Provisional application No. 62/181,331, filed on Jun. 18, 2015.

(51) Int. Cl.
| | | |
|---|---|---|
| *A61M 16/00* | (2006.01) | |
| *A61M 37/00* | (2006.01) | |
| *A61M 16/06* | (2006.01) | |
| *A61M 31/00* | (2006.01) | |
| *A61M 15/08* | (2006.01) | |

(52) U.S. Cl.
CPC .......... *A61M 37/00* (2013.01); *A61M 15/085* (2014.02); *A61M 16/0666* (2013.01); *A61M 31/002* (2013.01); *A61M 2202/0208* (2013.01); *A61M 2205/02* (2013.01)

(58) Field of Classification Search
CPC ................ A61M 37/00; A61M 15/085; A61M 16/0666; A61M 31/002; A61M 2205/02; A61M 2202/0208
See application file for complete search history.

(56) References Cited

U.S. PATENT DOCUMENTS

| | | | | | |
|---|---|---|---|---|---|
| 2,264,153 | A | * | 11/1941 | Rowe ................... | A61M 15/08 128/204.12 |
| 2,277,390 | A | * | 3/1942 | Crespo ................. | A61M 15/08 128/204.12 |
| 3,463,149 | A | * | 8/1969 | Albu ..................... | A61F 5/56 128/204.12 |
| 3,747,597 | A | * | 7/1973 | Olivera ................ | A62B 23/06 128/206.11 |
| 5,947,119 | A | * | 9/1999 | Reznick ............... | A62B 23/06 128/204.12 |
| 6,015,425 | A | * | 1/2000 | Altadonna, Jr. ...... | A61M 15/08 128/206.11 |
| 6,386,197 | B1 | * | 5/2002 | Miller .................. | A61F 5/08 128/200.24 |
| 6,561,188 | B1 | * | 5/2003 | Ellis .................... | A61M 3/0262 128/203.22 |
| 7,055,523 | B1 | * | 6/2006 | Brown ................. | A61F 5/08 128/206.11 |

(Continued)

*Primary Examiner* — Steven O Douglas
(74) *Attorney, Agent, or Firm* — Frances C. Hand; Carella, Byrne et al.

(57) ABSTRACT

In one embodiment, the nasal clip is infused with a volatile medicant and/or therapeutic aromatic that volatilizes under body temperature to permeate into the septum mucosa of a user's nose. In a second embodiment, the nasal clip has limbs that are pre-stressed to engage the septum mucosa so that the intermittent stimulation caused by the frequency of each heart beat and the heat in the inhaled warm breath help release the volatile medicants and aromatic materials. In a third embodiment, the nasal clip is integrated with an oxygen delivery cannula to allow delivery of oxygen with the medicant and/or therapeutic aromatic.

18 Claims, 11 Drawing Sheets

(56) References Cited

U.S. PATENT DOCUMENTS

| | | | |
|---|---|---|---|
| 7,108,198 B2* | 9/2006 | Altadonna, Jr. | A61K 9/0043 128/200.24 |
| 8,246,647 B2* | 8/2012 | Wien | A61F 5/08 606/199 |
| 9,272,117 B2* | 3/2016 | Miledi | A61M 21/02 |
| 2002/0153007 A1* | 10/2002 | Davi | A61M 15/08 128/200.24 |

* cited by examiner

TRANSDERMAL STIMULATOR AND MEDICANT MEDICAL DELIVERY DEVICE

This application claims the benefit of Provisional Patent Application 62/181,331, filed Jun. 18, 2015.

This invention relates to a transdermal stimulator and medicant medical delivery device.

As is known from U.S. Design Pat. 375,552, nasal clips have been constructed with a pair of limbs that are spaced apart for insertion in a nose of a user.

It is an object of the invention to deliver a medicant to a user in a non-invasive manner.

It is another object of the invention to deliver a therapeutic aroma to the nose of a user in a simple expeditious manner.

It is another object of the invention to provide a simple device for simultaneously delivering oxygen and medicant to a patient.

Briefly, the invention provides a delivery device in the form of a nasal clip for insertion in a nose of a user comprised of a connector, a pair of limbs extending from the connector and a pair of bulbous portions each at the free end of a limb. When placed in use, the limbs of the nasal clip are inserted into the nasal passages of the nose of a user and the bulbous portions engage opposite sides of the cartilaginous septum of the nose In one embodiment, the nasal clip is characterized in being made of a heat sensitive plastic having a volatile material infused therein, such as at least one of a volatile medicant and a volatile therapeutic aromatic material. When in use, as the user breathes, warm air passing into the nose heats the limbs and bulbous portions of the clip thereby causing the infused volatile material to volatilize and pass into the nose.

In another embodiment, the bulbous portions are biased towards each other for engagement with septum mucosa thereby causing dilation of the blood vessels in the nose of a user under a pre-stress. In this embodiment, when the nasal clip is inserted in a nose, the bulbous portions press against the septum mucosa and provide for an intermittent stimulation due to blood pulsing through the now dilated blood vessels with the frequency of each heart beat.

When inserted into the nose of a user, the body heat of the user transmitted through the septum mucosa activates the heat sensitive plastic of the bulbous portions which, in turn, activates a controlled release of the medicant and/or therapeutic aromatic material therein in a vaporous form for inhaling into the user.

In another embodiment, each said bulbous portion is constructed to function as a transdermal deliverer of a volatile material. To this end, each bulbous portion contains a reservoir chamber for receiving the volatile material, a grid disposed over the chamber to deliver the volatile material from the chamber and a porous membrane disposed over the grid to diffuse the volatile material therefrom into the septum mucosa.

The invention also provides a medical device for insertion in a nose of a user for delivery of oxygen as well as for delivery of a volatile material thereto, such as a medicant and/or therapeutic aromatic.

This medical device is comprised of a nasal cannula of conventional construction having a pair of tubes for positioning in and delivering oxygen to a pair of nasal passages of the nose of a user and a nasal clip mounted between the tubes of the nasal cannula that is constructed in accordance with any one of the above three embodiments.

These and other objects and advantages of the invention will become more apparent from the following detailed description taken in conjunction with the accompanying drawings wherein.

Figure 1:
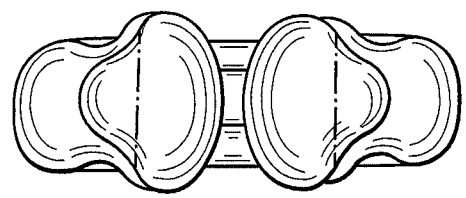
FIG. 1 is a top view of a PRIOR ART ornamental nasal clip.
Figure 2:
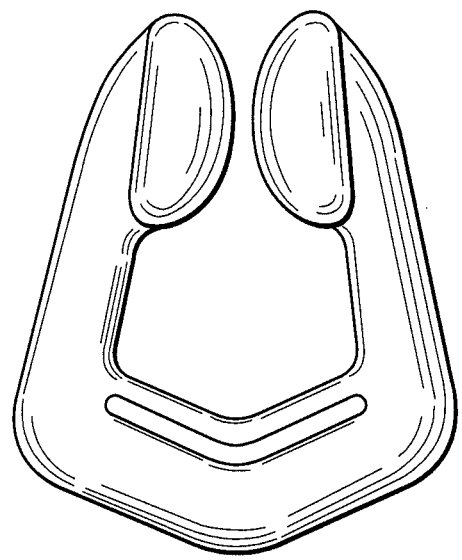
FIG. 2 is a plan view of the PRIOR ART ornamental nasal clip shown in FIG. 1.

Referring to FIGS. 1 and 2, a nasal clip is known from U.S. Design Pat. 375,552 wherein a pair of limbs connected to a connector to form a V-shape are separated at the free ends by a gap.

Referring to FIGS. 3 to 6, the nasal clip 200 is of one piece construction for insertion in a nose of a user and is made of a heat sensitive medical grade memory based thermoplastic that is molded into the final shape.

As illustrated, the nasal clip 200 has a connector 36, a pair of limbs 38, 39, each of which extends integrally from a respective end of the connector 36 in a direction towards the other of limb 38, 39 for positioning in a nasal passage of the nose of a user; and a pair of bulbous portions 48, 49, each of which is disposed on an end of a respective limb 38, 39 and is biased into contact with the other bulbous portion 48, 49 for engagement with the septum mucosa in the nose of a user.

The bulbous portions 48, 49 are three-dimensional portions and are preferably partial cylindrical/elliptical sections. There is no gap between bulbous portions 48, 49 and the bulbous portions 48, 49 are preferably pre-spring loaded with a specific spring load generated by a fixtured inward preload as described below.

Figure 7:
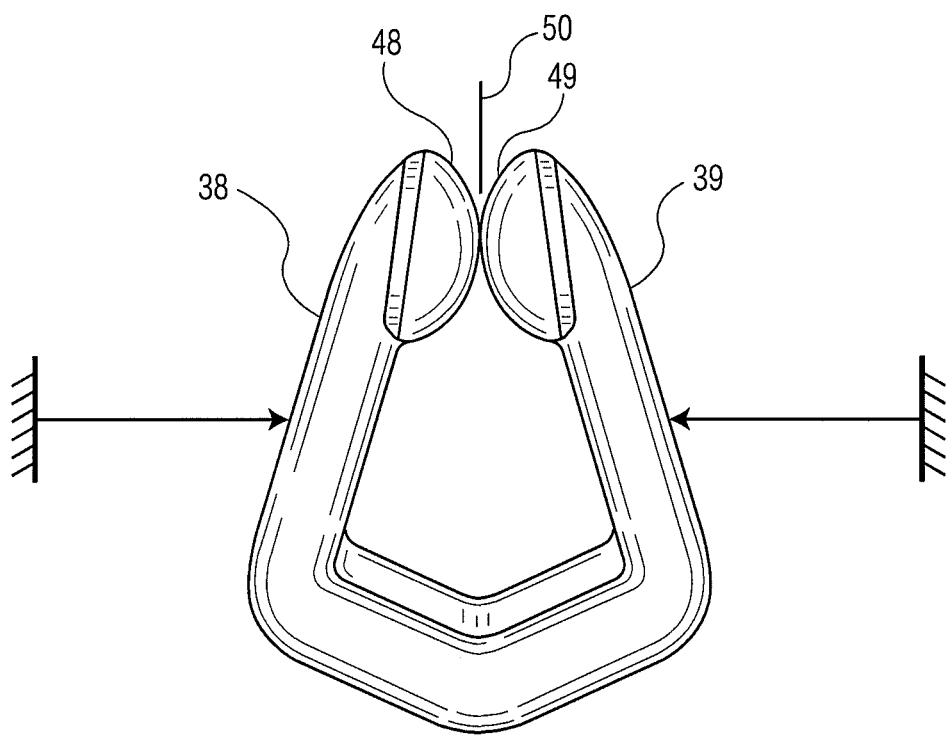
FIG. 7 illustrates a frontal plan view of the device shown in FIG. 3 with an inward fixture preload force.

Referring to FIG. 7, wherein like reference characters indicate like parts as above, the limbs 38, 39 of the clip 200 are pre-spring loaded with a specific post molded spring load generated by a fixture inward applied force of 0.150 kg per side on the limbs 38, 39 that generates a specific inward pressure on the bulbous portions 48, 49 immediately after the clip 200 has been molded. The fixture applied force is maintained while the clip is allowed to cool to room temperature, preferably to 70° F.

The specific pressure on the limbs 38, 39 is permanently maintained after cooling and after the clip 200 is removed from the fixture so that the bulbous portions 48, 49 are pre-stressed into contact with each other.

Figure 8A:
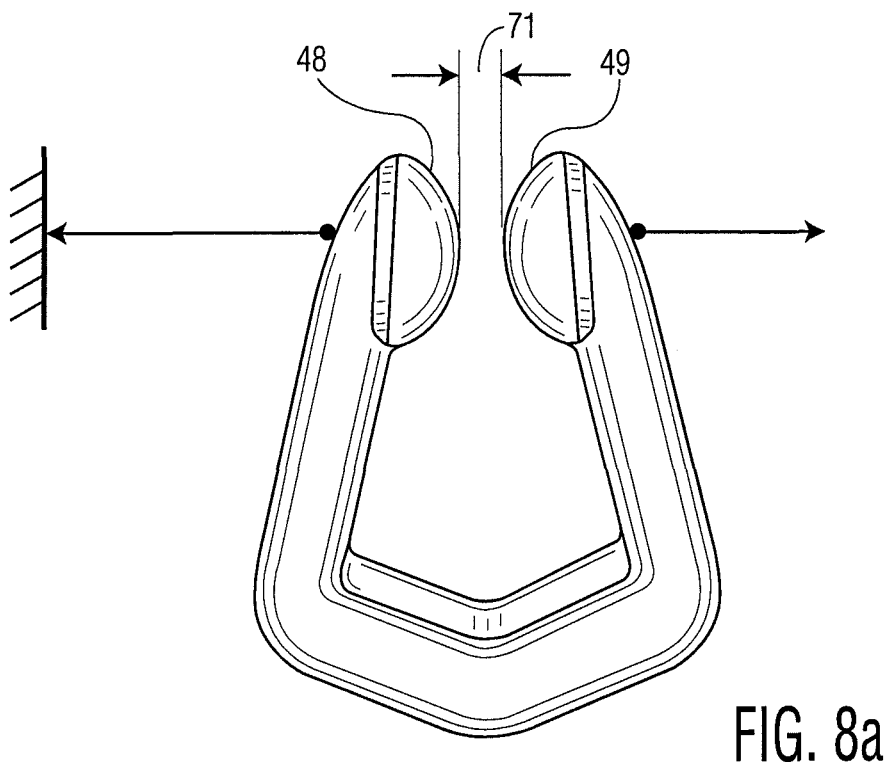
FIG. 8a illustrates a frontal plan view of the device shown in FIG. 3 with an opposing outward force applied.

Referring to FIG. 8a, in order to open the clip 200 for insertion into a nose, the bulbous portions 48, 49 are spread apart manually. As illustrated, a specific outward load A, for example of 0.022 kg, pulls outwardly at the bulbous portions 48, 49 to create a gap 71 between the bulbous portions 48, 49, for example not more than 0.010 inches at 70° F. During this time, the clip 200 is elastically deformed by the pulling of apart of the opposed bulbous portions 48, 49. At this time, the inherent resiliency of the clip 200 causes the limbs 38, 39 to be spring-biased towards each other to close the gap.

Figure 8B:
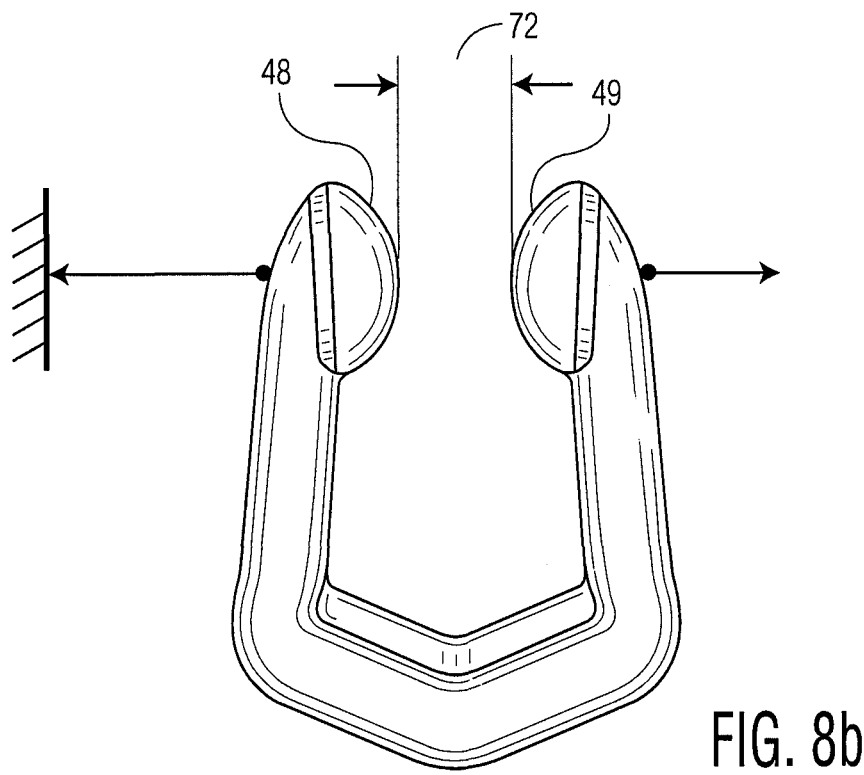
FIG. 8b illustrates a frontal plan view similar to FIG. 8a wherein a greater opposing outward force is applied than in FIG. 8b.

FIG. 8b shows a specific greater outward load B pulling outwardly at the bulbous portions 48, 49 to create a larger gap 72 than the gap 71 generated by the load A (FIG. 8a). The gap 72 is larger than the space to engage a nasal septum (not more than 0.250 inches) with a specific spring load. Under this load, the limbs 38, 39 become elastically deformed into a generally parallel relation.

When the outward pulling load A or B is released, the bulbous portions 48, 49 spring back into a pressured contact as shown in FIG. 7 wherein the contact is that of the post molded/post fixtured specific inward spring pressure measured at a room temperature of 70° F.

Figure 3:
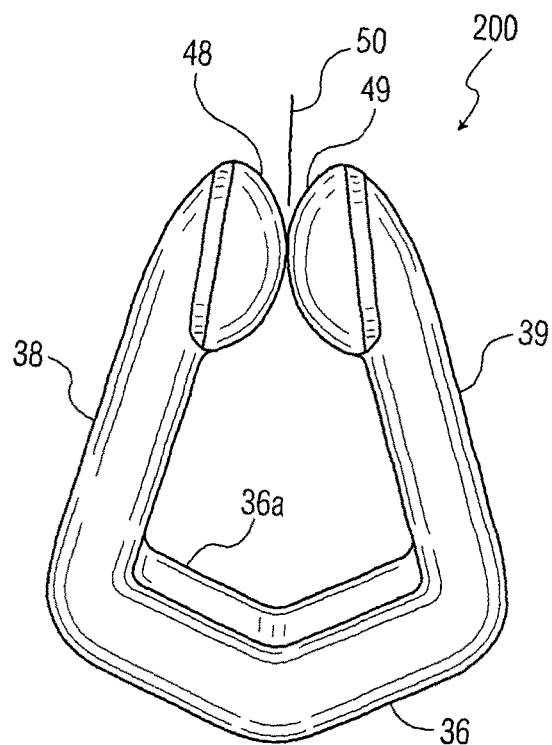
FIG. 3 illustrates a front plan view of a first preferred embodiment of a multi-functional delivery device in accordance with the invention.
Figure 4:
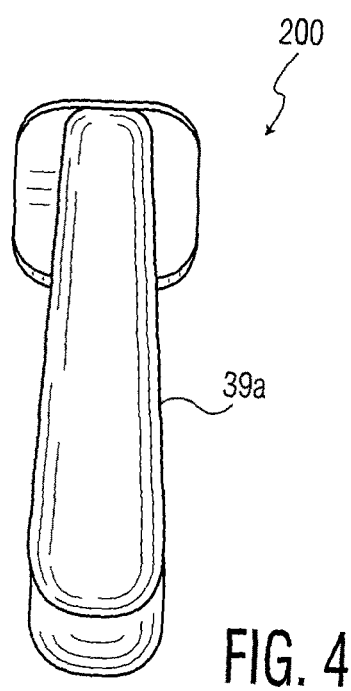
FIG. 4 illustrates a side view of the device shown in FIG. 3.
Figure 5:
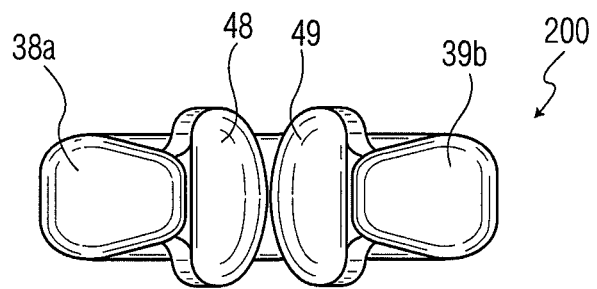
FIG. 5 illustrates a top view of the shown in FIG. 3.
Figure 6:
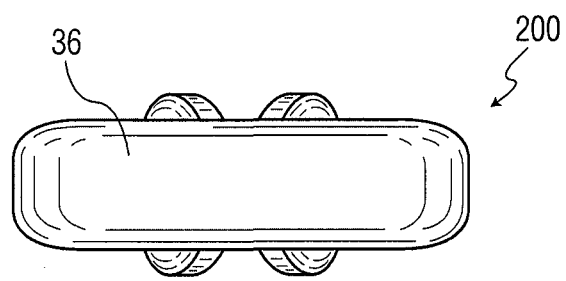
FIG. 6 illustrates a bottom view of the device shown in FIG. 3.

The generally V shape of the clip 200 as shown in each of FIG. 3, FIG. 7 and FIG. 8a is preferred, although any shape wherein the opposed bulbous portions 48, 49 that engage opposite sides of the septum to retain the clip 200 in the nose is within the scope of the invention.

The nasal clip 200 is characterized in being made of a heat sensitive plastic having a volatile material infused therein, such as at least one of a volatile medicant and a volatile therapeutic aromatic material.

The heat sensitive medical grade thermoplastic is a polyethylene sold under the name PREMOLYNE and model 1004-7829032-104 by Richlind Industries of Paramus, N.J. Other heat sensitive medical grade thermoplastics that may be used are Polystyrene, Polypropylene, Polyvinyl Chloride, Silicon and Polyethylene.

Figure 9:
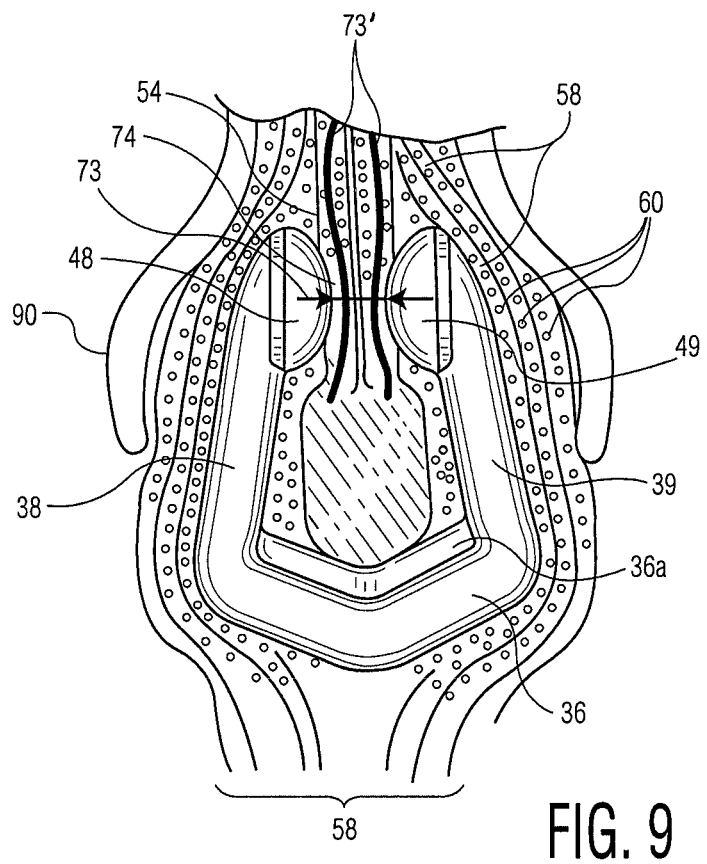
FIG. 9 illustrates a cross-sectional view orthogonal to the view shown in FIG. 10, taken along line 9-9 in FIG. 10 showing the device installed in a wearer's nose.
Figure 10:
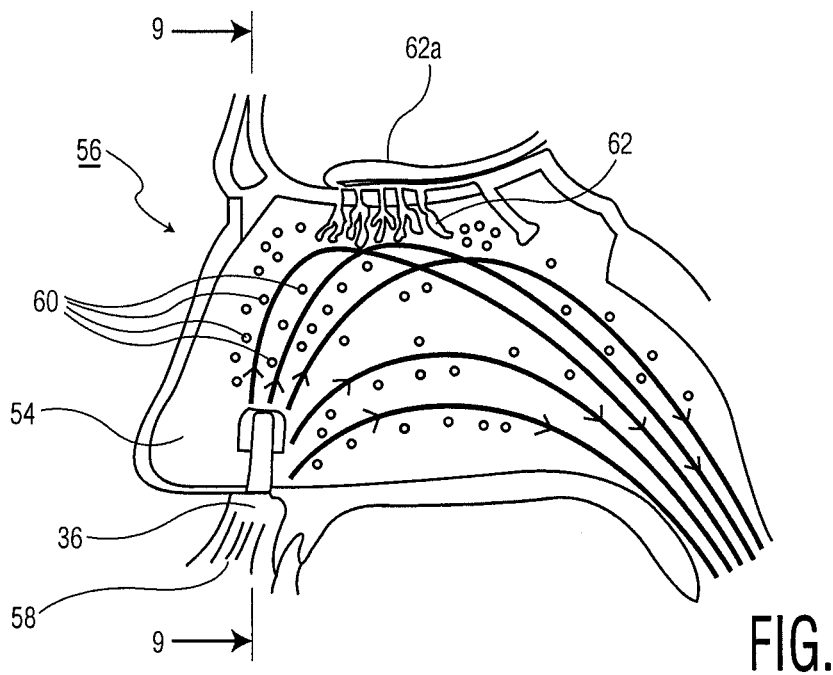
FIG. 10 illustrates is a first vertical cross-sectional view of the device shown in FIG. 3 showing the device installed in a wearer's nose.

Referring to FIGS. 9 and 10, when the nasal clip 200 is inserted into the nose 90 of a user, the bulbous portions 48, 49 engage opposite sides of the cartilaginous septum 74 in the area of the olfactory epithelium, trigeminal nerve bundle and nasal mucosa 73, 74 of the wearer's nose as simply applied by the wearer. Thereafter, during use, vaporized mendicants and/or aromatic materials 60 are transferred from the clip 200 to the wearer's olfactory sensors 62 by inhaled warmed breath 58.

In addition, via a transdermal action, the vaporized mendicants are osmotically absorbed into the mucosa and bundle of blood vessels 54 (FIG. 10) at the contact areas of the bulbous portions 48, 49 thereby breaking the blood/brain barrier through the blood vessels 54.

Preferably, the bulbous portions 48, 49 are opened to a gap 73 to engage the septum at the mucosa 74 and provide for an intermittent stimulation due to blood pulsing through the now dilated blood vessels 54 with the frequency of each heart beat caused by the inward preloaded spring pressure of the deformed clip 200 when opened.

The generally V shape of the clip 200 is presently preferred, although any shape may be used wherein the opposed portions 48, 49 engage opposite sides of the septum to retain the clip 200 in the nose with a specific pressure on the mucosa 74 which contains bundled blood vessels 54 and to retain the clip 200 on the septum at the mucosa 74 under a specific elastic force to intermittently stimulate the trigeminal nerves and dilate the pulsing blood vessels while breaking the blood/brain barrier through the walls of the dilated blood vessels.

Figure 12:
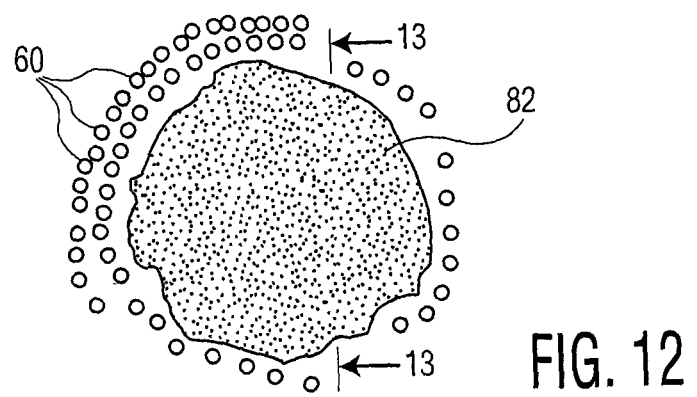
FIG. 12 illustrates a highly magnified cross-sectional view taken along line 9-9 in FIG. 9 showing a representation of the microscopic structural matrix of the material used to form the device shown in FIG. 3.

Referring to FIG. 9, the flexing of the free limbs 38, 39 occurs while the clip 200 is opened to insert on to the septum mucosa. The intermittent stimulation caused by the frequency of each heart beat and the heat in the inhaled warm breath 58 on the bulbous portions 48, 49 help increase the shifting of the inner matrix core of the clip throughout the clip 200, increase the pressure inside of the matrix (see FIG. 12) and help release the volatile medicants and aromatic materials 60 to continuously escape from the clip 200.

The medicants and aromatic materials 60 that are continuously released and given off by the clip 200 are entrained in the warm inhalations into the nasal cavities 90 (see FIG. 9) and the contact areas 74 which are additionally warmed by the bundle of blood vessels 54 on the inner mucosa 74 on which the clip 200 is in contact.

The matrix structure (FIG. 12) of the plastic used to form the clip 200 heats to body temperature when placed on the septum mucosa 74 thereby activating the heat sensitive memory based medical grade plastic material to the human body temperature of approximately 98.6° F. which, in turn, activates the controlled release of the infused medicants and/or aromatic materials in a sufficient vaporous form 60.

FIG. 10 shows the controlled inhalation release of volatile aromatic material along with a portion of volatile medicants conveyed thereby to the wearer's olfactory sensors (receptors) 62 to create a sufficient desired aromatic/medicant sensation providing the desired therapeutic delivery and proper administration of the aromatic material and/or medicants by way of the olfactory system 62, 62a to the various sections of the brain that can benefit from olfactory deliverance of the therapeutic deliverance of the therapeutic effect to the body.

Figure 11A:
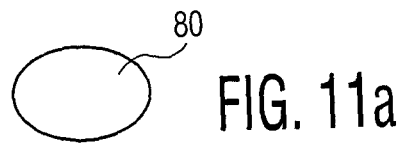
FIG. 11(a) illustrates a front plan view of a typical resin bead used to form the devices shown in FIG. 3 and in FIG. 15.
Figure 11B:
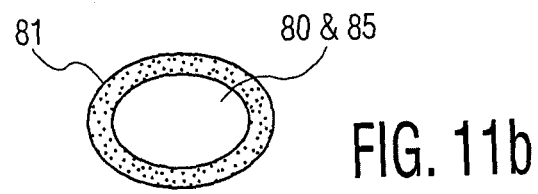
FIG. 11(b) illustrates a front plan view of the resin bead shown in FIG. 11(a) after being uniformly coated (prior to molding) with a medicant and/or aromatic material used to form the devices shown in FIG. 3 and in FIG. 15.

FIG. 11a shows a resin bead 80 for making the nasal clip 200 and FIG. 11b shows a resin bead 80 uniformly coated with a specific measured amount of the medicants and/or the aromatic material 81. The coated resin bead 80 is used as a component material in the manufacture of the clip 200, for example, by typical injection molding processes and the like.

The unique uniform coating process is described as follows:
  Weigh a batch of resin beads 80 needed to manufacture the desired quantity of clips 200;
  Mix in the medicants and/or the aromatic material 81, for example, in an amount of from 1% to 10% by weight, and in the form of oils, essential oils, G.R.A.S. oils, hemp oils, cannabis oils, concentrated solutions, tinctures, volatiles, aromas, crystals, powders, holistic natural organics, and/or prescription drugs; and
  Measure and mix in an amount of volatile compatible solutions which are more volatile than the medicants, for example, in an amount of from 0.025% to 1% by weight, in order to facilitate volatilizing of the medicant or therapeutic aromatic.

The medicants 81 are formulated to be compatible with the existing plasticizers of the resin beads 80 and are added, mixed, uniformly coated and blended in pre-determined mixtures by preferably placing the resin beads 80 in a mechanical tumbler mixer; adding a measured medicant solution and tumbling over a period of time to insure a uniform coating of each bead 80.

The coated beads are allowed to dry at room temperature over an adequate time, for example, within 72 hours, to avoid "clumping" of the beads.

The coated resin beads are then injection molded at an adequate melt temperature as recommended by the resin material supplier. The medicant should not degrade in the resin melt temperature recommended range.

The injection molded process sufficiently traps, infuses and permeates the medicant into the medical grade memory based thermoplastic matrix 82 (FIG. 12) after the molding and cooling of the nasal clip 200 of FIG. 3.

Figure 13:
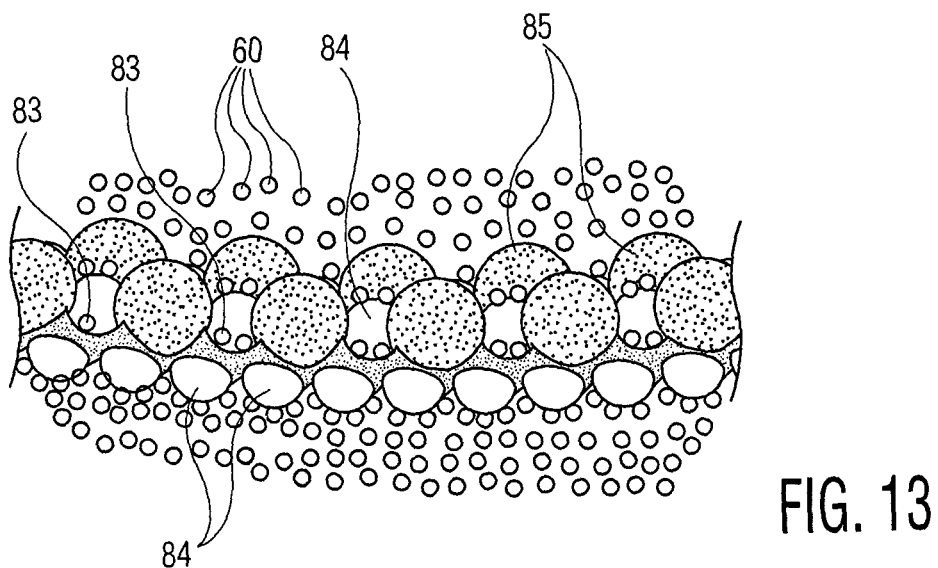
FIG. 13 illustrates a further highly magnified microscopic cross-sectional view taken along 13-13 in FIG. 1.

FIG. 13 illustrates a microscopic chain representation of various molecular components including the loosely bonded volatile medicants 83, tighter bonded less volatile plasticizers 84, and non-volatile plastic resin 85 which make up the structural matrix 82 of the material used to form the nasal clip 200 shown in FIG. 3.

The preferably loosely bonded volatile medicant solutions 83 will constantly release from the original less volatile plasticizers 84 and from the heat sensitive plastic material 85 which forms the nasal clip 200 (FIG. 3) as the clip is molded, cooled and cured during the normal conventional molding process.

In this respect, it is known that the plasticizers 84 used in injection molding of resins will volatilize out of the molded resin over time. The volatile material (e.g. medicant and therapeutic aromatic material) of the invention has a greater volatility than the plasticizers 84 under normal body temperatures, e.g. 98.6° F.

The volatile materials that may be delivered by the clips 200 include prescription drugs/pharmaceuticals, such as, but not limited to:
  Nicotine to control cigarette addiction.
  Medical marijuana to relieve effects of glaucoma, chronic pain, epilepsy, severe nausea, persistent muscle spasms, sleep disorders, post-traumatic stress disorders and relief from severe opiate and alcohol withdrawal.
  Diclofenac Epolamine an anti-inflammatory drug which is a pain killer that includes aspirin, Advil®, Motrin® (ibuprofen), Aleve® and Naprosyn® (naproxen) prescribed for pain from sprains muscle strains and other minor injuries.
  Fentanyl used to treat moderate to severe chronic pain.
  Nitroglycerin sometime prescribed for the treatment of angina in lieu of sublingual pills.
  Insulin or any other diabetic medicant to treat diabetes.

Figure 14:
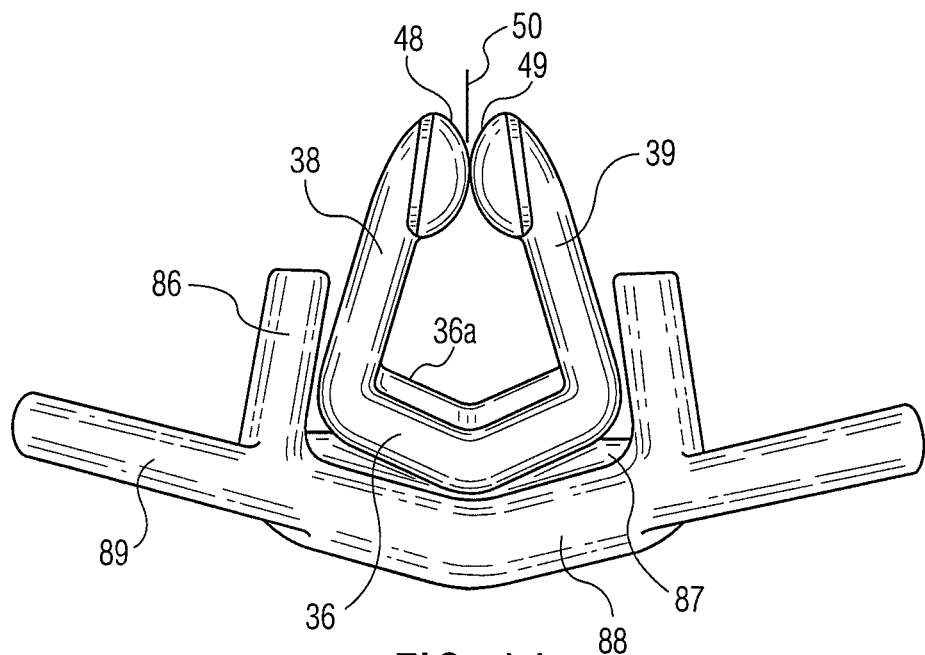
FIG. 14 illustrates a front plan view of a second embodiment of a nasal cannula multi-functional oxygen/medicant delivery device in accordance with the invention.
Figure 15:
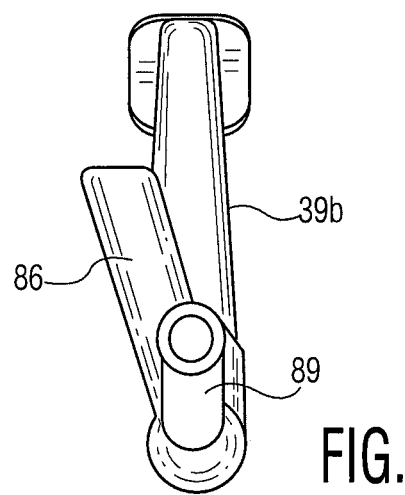
FIG. 15 illustrates a side view of the device shown in FIG. 14.
Figure 16:
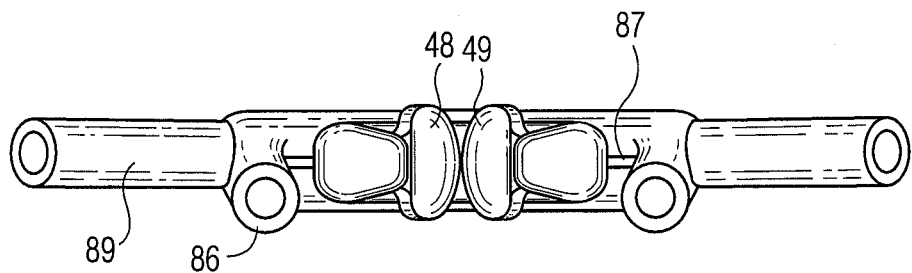
FIG. 16 illustrates a top view of the device shown in FIG. 14.

Referring to FIGS. 14 to 16, wherein like reference characters indicate like parts as above, the clip 200 is combined with a nasal cannula for the delivery of oxygen to form a medical device for the nasal delivery of medicant and/or a therapeutic aromatic and oxygen. As shown, the clip 200 is disposed between the two tubular outlets 86 of the cannula so that a medicant may be delivered with oxygen.

As illustrated in FIG. 14, the nasal cannula has two tubular outlets or prongs 86 which are to be placed in the nostrils 90 of a user (see FIG. 17) and from which a mixture of air and oxygen flows.

The nasal cannula is also connected via inlet tubes 89 to an oxygen supply, such as a portable oxygen generator or a wall tube hooking around a patient's ears or by an elastic head band. A gusset 87 extends between the outlets 86 to which the clip 200, as in FIG. 3 or FIG. 7 is integrally attached.

The most common form of adult cannula carries 1-5 liters of oxygen per minute. Flow rates of up to 60 liters of air/oxygen per minute can be delivered through a wider bore humidified nasal cannula. Cannulae with smaller prongs intended for infant or neonatal use can carry less than one liter per minute.

Figure 17:
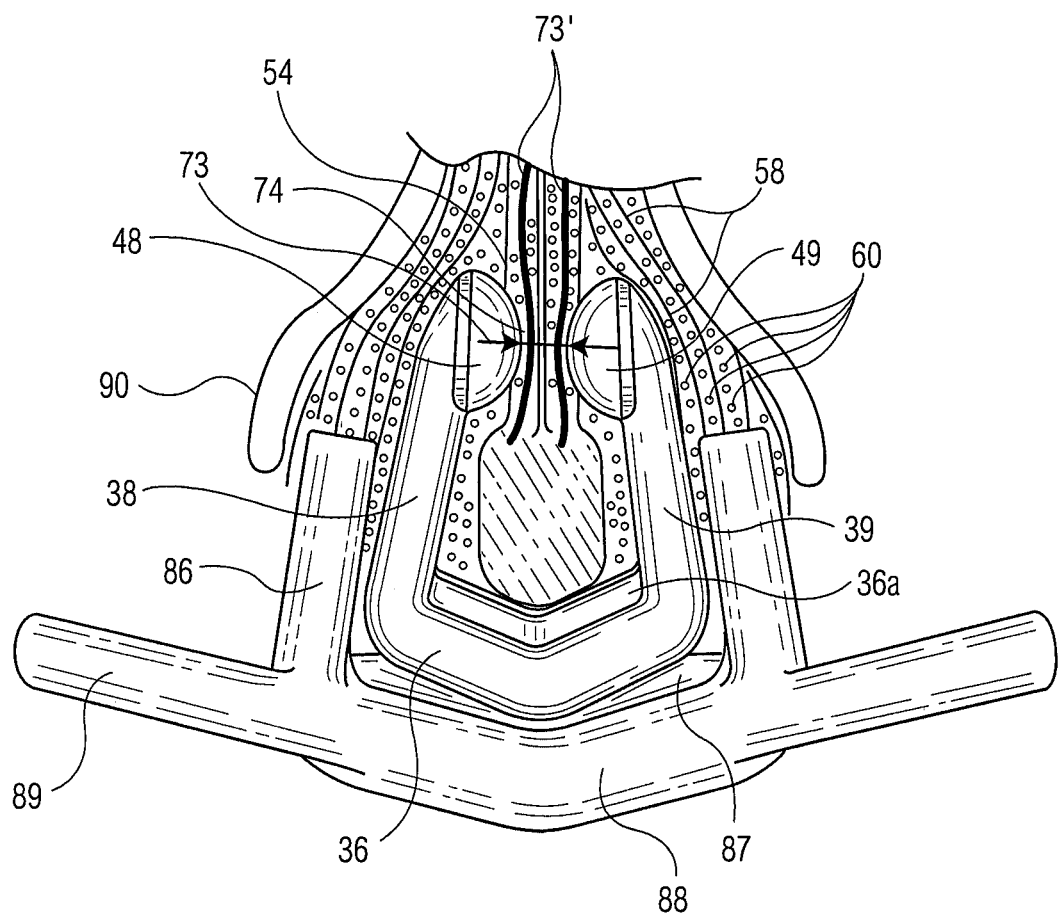
FIG. 17 illustrates a view of the device of FIG. 14 in a nose of a user.
Figure 18:
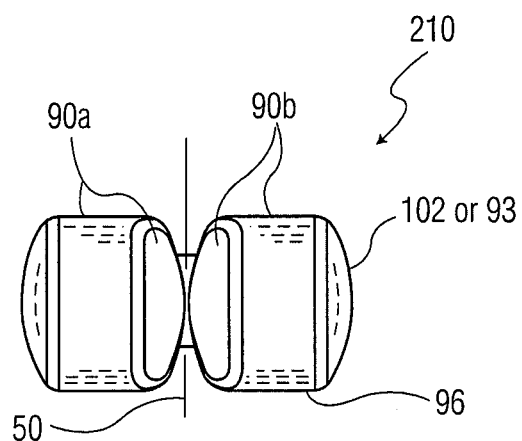
FIG. 18 illustrates a top view of a nasal clip for transdermal transfer of a volatile material in accordance with the invention.

FIG. 17 illustrates the transfer of vaporized mendicants and aromatic materials 60 from the clip 200 to the wearer's olfactory sensors 62 by inhaled warmed breath 58 and the delivery of air/oxygen conveyed through the inlet and outlet tubes 86, 88 & 89 of the cannula. FIG. 17 also shows the transdermal action of the mendicants osmotically absorbed into the mucosa and blood vessel bundle 73' breaking the blood/brain barrier through the walls of the blood vessels 73'. Flexible feed tubes normally connected to the inlet tubes 89 generally required to feed the air/oxygen from its source are not shown in FIG. 17.

Referring to FIGS. 18 to 21, wherein like reference characters indicate like parts as above, the nasal clip 210 may be constructed to facilitate transdermal delivery of a volatile material to the nose of a user and is intended to be activated by the intranasal temperature of 98.6° F. Further, the nasal clip 210 may be combined with a nasal cannula as in FIGS. 14 to 16 to also deliver oxygen to a user.

The nasal clip 210, as above, has a connector 36, a pair of limbs 38, 39 and a pair of bulbous portions 90a, 90b.

Each bulbous portion 90a, 90b is disposed on an end of a respective limb 38, 39 and is biased into contact with the other bulbous portion for engagement with septum mucosa in the nose of a user.

The bulbous portions 90a, 90b are of like construction. Hence, only the bulbous portion 90b will be described in detail.

Figure 23:
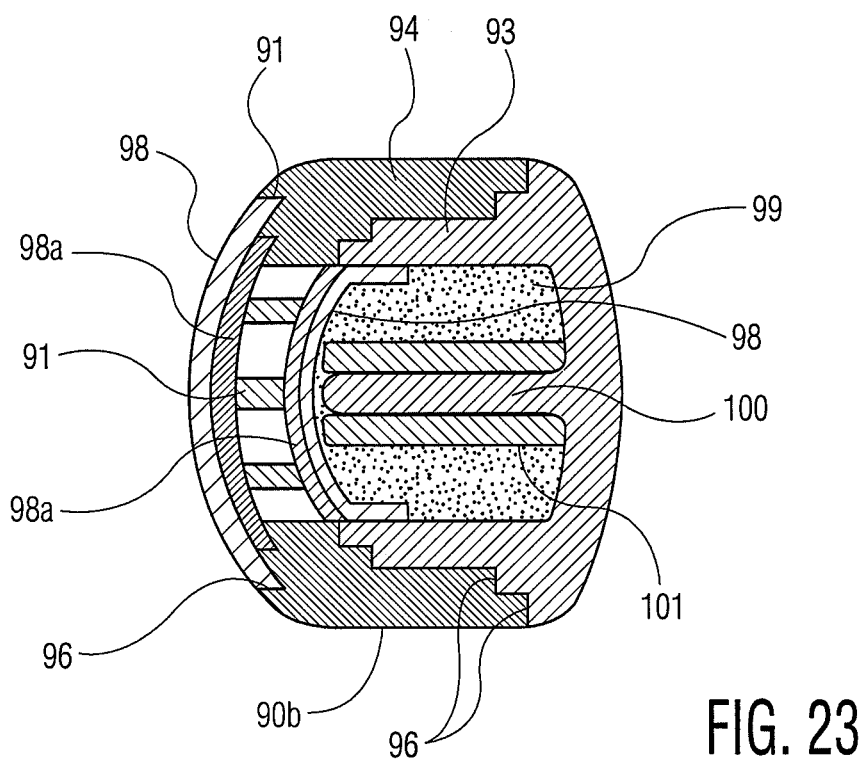
FIG. 23 illustrates a cross-sectional view of a bulbous portion of the nasal clip of FIG. 18 taken on line 23-23 of FIG. 19.

Referring to FIG. 23, the bulbous portion 90b is made of two parts 93, 94 that mate with each other. The female part 94 is integral with the limb 39 and the male part 93 is separately fitted onto the female part 94 to complete the assembly.

The male part 93 includes a reservoir chamber 99 for receiving at least one volatile material, e.g. an intended dosage of a prepared transdermal medicant.

The female part 94 includes a grid 91 in the face of the part 94 and disposed over the chamber 99 to deliver the volatile material from the chamber 99. In addition, an absorbent pad 98*a* is disposed over the grid 91 for absorbing the volatile material from the chamber 99 and a porous membrane 98 is disposed over the absorbent pad 98*a* for releasing the volatile material into the nose of a user.

As illustrated, the partial cylindrical/elliptical surface of the female part 94 has a partial cylindrical/elliptical recess 97 which nest and locate the porous membrane 98 and absorbent pad 98*a*.

In addition, the female part 94 has a second absorbent pad 98*a* between the grid 91 and the reservoir chamber 99 and a second porous membrane 98 between the second absorbent pad 98*a* and the reservoir chamber. Also, the male part 93 has a centrally located post 100 and a cylindrical wick 101 supported on the post to extend through the reservoir chamber 99 to the second porous membrane 98 for conveying volatile material from the reservoir chamber 99 to the second porous membrane 98 and beyond.

The two parts 93, 94 are secured to each other by ultrasonic welding at several places 96.

The absorbent backing pad 98*a* (which can be optionally used as a pad made up of a gelled medicant) helps diffuse a medicant from the reservoir chamber 99 and the slightly larger overlaying outer porous membrane 98 meters the medicant to the septum mucosa 74.

The space sandwiched between the outer absorbent backing pad 98*a* and the inner absorbent pad 98*a* (the space between the openings of the open grid baffle 91) can also be used to store the transdermal medicant as a gel or liquid.

The male part 93 can be filled with a measured amount of the preferred medicant and inserted into the female part 94 and ultrasonically welded at various places 96 to seal/enclose the medicant in the reservoir chamber 99 forming a unique transdermal delivery system.

A second method of filling the medicant into the enclosed reservoir chamber 99 is to complete the assembly described above inserting the empty reservoir male part 93 into the preassembled female part 94 and ultrasonically welding at various places 96 sealing the empty reservoir chamber. Then, a hypodermic needle (not shown) filled with the measured amount of the preferred prepared transdermal medicant may be inserted through the base of the male part and the medicant injected into the reservoir chamber 99 with the prescribed dosage. Closure of the opening into the reservoir by the needle may be accomplished by a plug, self-closing by the material of the male part or the like.

A third method of filling the transdermal medicant into the clip 210 utilizes gel pads 98*a* that are heat sensitive to be dissoluble at 90° F. to prevent the heat sensitive transdermal medicant from prematurely flowing out of the clip 210 when stored at room temperature and not applied in a nose.

In accordance with this third method, the open grid 91 is filled with the heat sensitive medicant which is prepared at a consistency of honey at 70° F.

Thereafter, a second amount of transdermal medicant in the form of a heat sensitive dissolvable (preferably dissolvable at 90° F.) gel pad 98*a* is placed over the previously filled open grid 91.

The porous membrane(s) 98 is then placed over the pad(s) and ultrasonically welded in place.

The assembly is completed as described above by inserting the male part 93 into the preassembled female part 94.

The reservoir chamber 99 can be pre-filled with a prepared heat sensitive transdermal medicant at preferably the consistency of water when at 70° F. and the parts 93, 94 ultrasonically welded at various places 96 sealing the reservoir chamber.

Another purpose of the third method is for the medical device to disburse the medicant outwardly in a controlled, continuous manner. Preferably, the lightest (consistency of water at 70° F.) heat sensitive transdermal medicant stored in the reservoir chamber, when heated by the intranasal temperature of 98.6° F. begins to expand and flows outwardly creating pressure against the gel pad(s) and the transdermal medicant trapped in the open grid 91. The medicants in the gel pad(s) and grid 91 then slowly dissolve and disperse in sequence.

In a fourth alternate method, the reservoir chamber could be empty then filled with the measured amount of the preferred prepared transdermal medicant injected via a hypodermic needle into the reservoir chamber 99.

Figure 24:
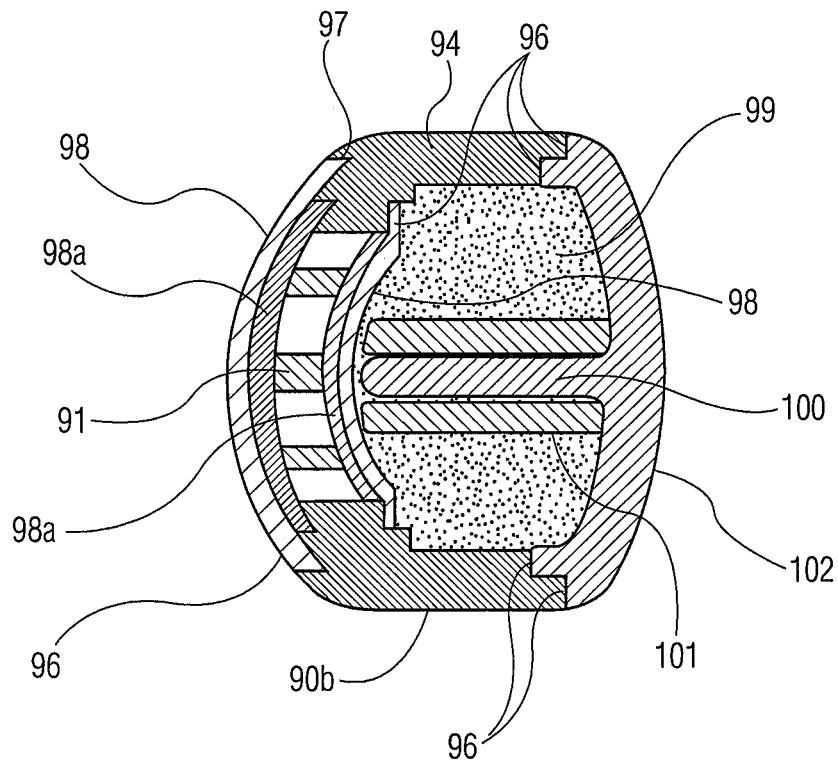
FIG. 24 illustrates a cross-sectional view of a modified bulbous portion of the nasal clip of FIG. 19.

Referring to FIG. 24 wherein like reference characters indicate like parts as above, the bulbous portion 90*b* may be made with a female part 94 and a closure cap 102 assembled in place of the male part 93. The use of the end closure cap 102 provides for a greater volume of medicant in the medicant reservoir 99.

Figure 25:
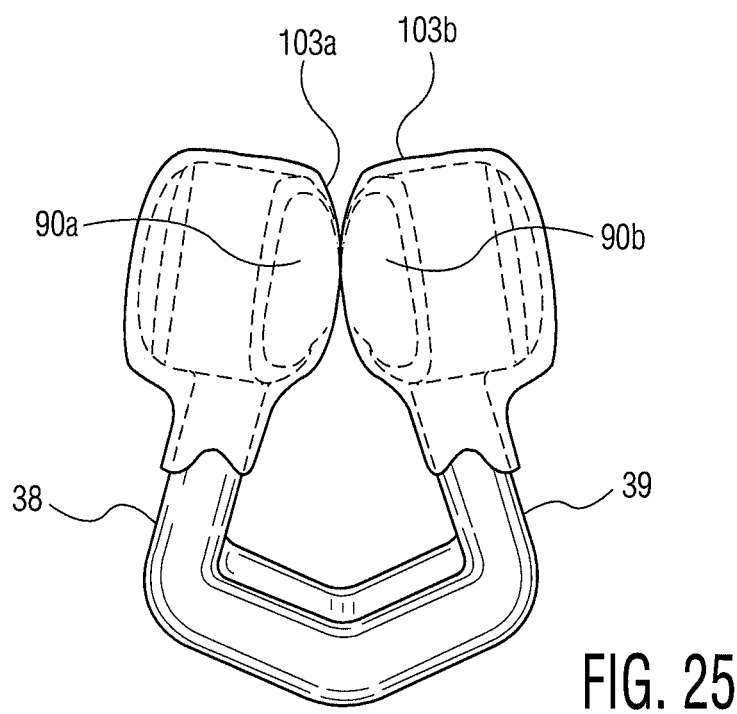
FIG. 25 illustrates a view of the nasal clip of FIG. 19 with non-porous protective covers over the bulbous portions.

Referring to FIG. 25, wherein like reference characters indicate like parts as above, after assembly, preferably thin inert non-porous removable liner(s) or heat shrinkable sleeve(s) 103*a*, 103*b* are applied over the bulbous portions 90*a*,90*b* and limbs 38, 39 to cover and temporarily seal each of the porous outer membranes 98 located on the outside surfaces of the bulbous portion 90*a*, 90*b* to avoid medicant leakage and maintain sanitized integrity of future skin contact areas and improving shelf life during storage.

The technology of the transdermal clip 210 is an improvement over prior art thermal patch technologies and other prior art products due to the fact that the transdermal dosage application areas are located "in the nose on the septum mucosa" which does not have a epidermal barrier and is thin and moist allowing controlled steady penetration/absorption and diffusion through the thin mucosa. The medicant(s) adsorbs into the blood vessels quickly breaking the blood brain barrier and allowing a greater variety of medications to be used transdermaly.

Adhesive and permeability enhancers and solvents are not needed in the clip 210 as the contact areas are secured in place by a specific spring pressure (similar to a light acupressure) which holds the clip 210 in place and which also stimulates the trigeminal nerve system and olfactory receptors expediting the delivery of the medicant to the brain thru the olfactory system while quickly breaking the blood brain barrier.

The spring pressure construction and location of the bulbous portions 90*a*, 90*b* are intended to provide a pressure/acupressure sufficient to transmit specific pressure 73 to the bundle of targeted blood vessels 54 in the nasal mucosa 74, to the maxillary nerve and to the infraorbital nerve. The unique structure and precise sufficient transition of spring pressure of the clip 200 (or clip 210) against the pulsing blood vessels 54 creates and provides for the intermittent stimulation of pressure receptors in the end segment of the ophthalmic branch of the trigeminal nerve and trigeminal nerve system which has also been described as a secondary olfactory system greatly accelerating olfactory receptor 62 signals to the olfactory system 62*a* and then to the brain. It is also well established that acceleration of normal neurological signals can be accomplished by external stimulation of nerves, particularly the intermittent repetition of stimulation of such nerves.

The trigeminal nerve: The trigeminal nerve is the largest cranial nerve in the central nervous system and passes over the "petrous apex" forming the Gasserian ganglion where the nerve divided into three branches. Two of these branches are of importance.

The ophthalmic branch of the trigeminal nerve controls sensation to the cornea, ciliary body, iris lachrymal gland, conjunctiva, nasal mucous membrane, eyelid, eyebrow, forehead and regions of the nose.

The nasal branch of the maxillary nerve and the infraorbital nerve passes into tissue lining the septum of the nose.

The sensory portion of the trigeminal nerve, the trigeminal sensory nucleus, the facial motor nuclei and the motor neuron of the facial nerve provide a feedback path for both complex and simple reflexes. These reflexes include sneezing and neurological stimulation of the nasal mucosa.

The prior art technique of transcutaneous electrostimulation of nerves (TENS) is based upon such intermittent stimulation. This use of electrical stimulators (electro stimulation technique) has helped epileptics have fewer seizures. Thus, one may infer that such a stimulation will inhibit reflexes that control the dilation of blood vessels in the nasal mucosa and thus reduce their swelling. The use and process of doctor applied electro stimulation—devices and in and out patient services medical treatments to apply the electro stimulation therapy is time consuming and expensive.

The unique sufficient spring structure of the clips 200, 210 on the nasal mucosa provides for the non-electric intermittent stimulation (due to intermittent stimulation caused by the blood pulsing through the dilated blood vessels 54 with the frequency of each heart beat) of pressure receptors in the end segment of the ophthalmic branch of the trigeminal nerves (based on the technique of (TENS). The use of the nasal clip 200, 210 when easily applied by the wearer achieves the same results as the electrostimulation devices without the need of expensive equipment or the presence of a doctor/technician. In addition to epileptics having fewer seizures, improved breathing occurs—if the clip is worn during sleep—nasal congestion (due to dilation), and sinusitis may also be relieved and sleep deprivation including chronic snoring may be reduced.

The unique structure of the nasal clip provides for sufficient transmission of stimulation without the use of electrodes or electrical stimulation on the nerves and through less invasive functions than using electrical stimulators which can help epileptics have fewer seizures.

In addition, the use and delivery of mendicants (normally prescribed to reduce seizures) incorporated into the nasal clip make the clip uniquely more effective due to the additional multiple simultaneous effect of the internasal matrix-transdermal and olfactory stimulation which is a unique multiple feature of the delivery system as described above.

Figure 19:
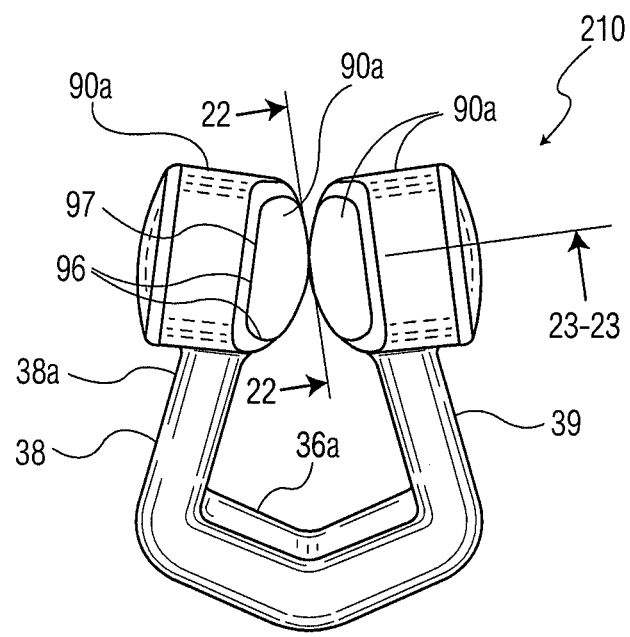
FIG. 19 illustrates a front view of the nasal clip of FIG. 18.
Figure 20:
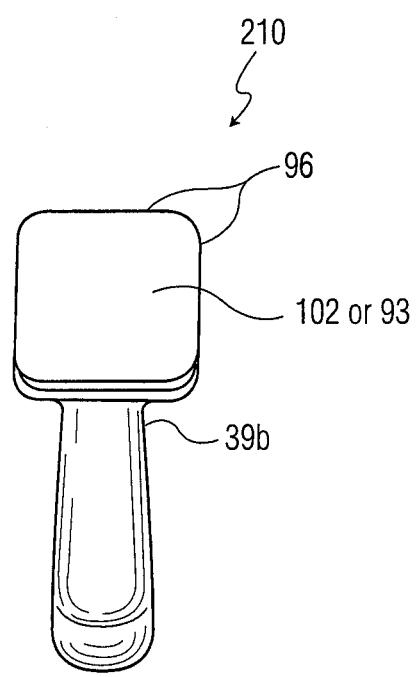
FIG. 20 illustrates a side view of the nasal clip of FIG. 18.
Figure 21:
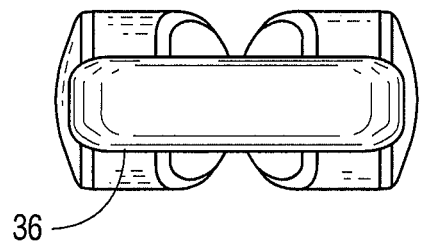
FIG. 21 illustrates a bottom view of the nasal clip of FIG. 18.
Figure 22:
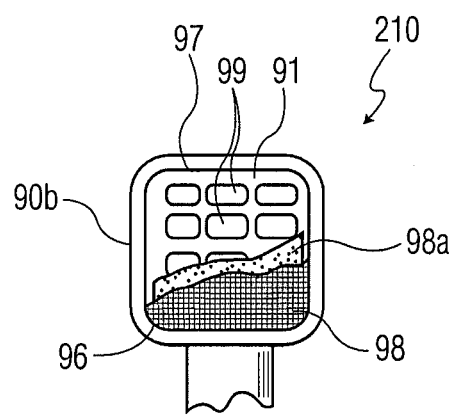
FIG. 22 illustrates a partial front view of a bulbous portion of the nasal clip taken on line 22-22 of FIG. 19.

Normally, pressure sensors adapt to neurological stimulation, and thus the constant pressure on the internal nasal branches of the infraorbital nerve would not act to inhibit portions of the trigeminal nerve. However, the unique spring structure of the nasal clips as shown in FIGS. 3 and 19 provides for a pressure which is sufficient to transmit specific intermittent stimulation of pressure receptors in the end segment of the ophthalmic branch of the trigeminal nerve as explained above.

The region where the bulbous portions 48, 49, 90a, 90b press the septum is well vacuolated. The lining of the septum contains alar branches of the lateral nasal artery. The pulsation of blood in these vessels 54 causes a variation of pressure after each systolic pulse, thus providing stimulation with each heart beat. For example, this is precisely the pulsation that one feels when the device is placed on a finger tip.

The time interval between stimulations, before one reaches adaption of the nerve, is much shorter than the time interval of the pressure application resulting from the periodic pressure application of the nasal clip spring due to the blood pulsation, namely, the time interval between stimulations, before one reaches adaptation, the neurological recovery is well under 500 milliseconds (the typical stimulation time used in evoked potential measurements is one stimulus per second).

Thus, the nasal clip acts, in essence, as a non-electro intermittent stimulator to a portion of the pressure receptors of the trigeminal nerve that inhibits autonomous secretion of mucosal plasma. This reduces dilation of arteries supplying blood to the nasal mucosa and increases airflow through the nasal passages and also accelerates signals to the olfactory receptors 62, olfactory bulb 62a and to various sections of the brain to quickly provide desired therapeutic results.

A secondary cause of reduction in the mucosal swelling is due directly to the average pressure of the nasal clip precise sufficient spring pressure 73 on this portion of the blood vessels 54, specifically the alar branches of the lateral nasal artery that provides perfusion to some of the nasal mucosa 74. This pressure reduces perfusion directly by flattening the blood vessels 54 and thus providing for an obstruction to blood flow.

When using the nasal clip, the combination of reduced perfusion and inhibited reflex explains the observed improvement of reduced nasal resistance can be and has been measured by acoustic rhinometric analysis (an instrument which measures nasal resistance).

The invention thus provides a medical device as shown is FIGS. 14-16 that is cost-effective and which requires greatly reduced maintenance as compared to prior art techniques for supplying oxygen and medicants to a patient.

The unique multi-functional medical device of FIGS. 14-16 will eliminate many of the flow rate and discomfort problems including limited flow rate problems existing in prior art conventional existing prior art cannulas. Most conventional cannulas only provide oxygen at low flow rates-up to 5 liters per minute (Umin.) and result in discomfort to the patient, drying of the nasal passages, and possibly nose bleeds (epistaxis). In cannulas with flow rates above 6 Um, the laminar flow becomes turbulent and the oxygen therapy being delivered is only as effective as delivering 5-6 Um. The medical device of FIGS. 14-16 allows effective flow rates above 6 Um (if needed). Further, this medical device has a positive effect providing nasal dilation and reduced nasal resistance. Thus, less oxygen can be used at lowered flow rates while achieving improved efficient oxygen dosage delivery to the patient.

The medical device 210 of FIGS. 14-16 provides for freer breathing due to enhanced trigeminal stimulation, reduced mucosal swelling, improved nasal dilation and reduced nasal resistance. In addition the nasal mucosa stays moist due to enhanced flow of mucus relieving previous stated discomfort to the patient, i. e. not limited to drying of the nasal passages, and nosebleeds (epistaxis). In this respect, the medical device 210 may provide relief to persons suffering from sleep apnea and, as such, would be more efficient and less cumbersome than apparati presently in use.

The medical device of FIGS. 14-16 also includes the feature of controlled oxygen enhancing mendicant delivery (see FIG. 18) using matrix medicants (as in the embodiment of FIG. 3) and/or transdermal medicants (as in the embodiment of FIG. 19) additionally thru trigeminal stimulation and olfactory stimulation 73' intending to improve efficient oxygen delivery in a unique way to sufficiently make oxygen delivery less evasive and more effective.

Simply adding a light sterile saline solution and/or other soothing moisturizing medicant into the transdermal reservoir chambers 99 of the embodiment of FIG. 19 can additionally help keep the inner nose moisturized with a controlled steady dosage and efficient delivery providing comfort and relieving discomfort of dry nasal passages and help relieve nosebleeds during oxygen therapy.

In addition, the specific structural spring loaded pressure against the septum helps hold the medical device in the nostrils, relieving irritation from the air/oxygen feed tubes pressure against the face ears and head which is an annoying experience when using prior art nasal cannulas.

What is claimed is:

1. A nasal clip for insertion in a nose of a user comprising
a connector;
a pair of limbs, each said limb extending integrally from a respective end of said connector in a direction towards the other of said pair of limbs configured for positioning in a nasal passage of the nose of a user; and
a pair of bulbous portions, each said bulbous portion being disposed on an end of a respective limb and biased into contact with the other of said bulbous portions and configured for engagement with septum mucosa in the nose of a user and
characterized in being made of a heat sensitive plastic having at least one of a volatile medicant and a volatile therapeutic aromatic material infused therein.

2. A nasal clip as set forth in claim 1 further comprising a gusset rib integral with said connector and connecting said pair of limbs together at a base thereof to form a one-piece structure.

3. A nasal clip as set forth in claim 1 wherein said pair of limbs define a V-shape.

4. A nasal clip as set forth in claim 1 wherein each bulbous portion has a cylindrical/elliptical shape.

5. A nasal clip for insertion in a nose of a user comprising
a connector;
a pair of limbs, each said limb extending integrally from a respective end of said connector in a direction towards the other of said pair of limbs configured for positioning in a nasal passage of the nose of a user; and
a pair of bulbous portions, each said bulbous portion being disposed on an end of a respective limb and biased into contact with the other of said bulbous portions and configured for engagement with septum mucosa in the nose of a user and including a reservoir chamber for receiving at least one medicant, a grid disposed over said chamber to deliver the medicant from said chamber and a porous membrane disposed over said grid to diffuse the medicant therefrom.

6. A nasal clip as set forth in claim 5 wherein said medicant is a volatile material.

7. A nasal clip as set forth in claim 5 wherein said medicant is a therapeutic aromatic material.

8. A nasal clip as set forth in claim 5 wherein each said bulbous portion includes an absorbent pad between said grid and said porous membrane for absorbing the medicant from said chamber for release through said porous membrane.

9. A nasal clip as set forth in claim 8 wherein each said bulbous portion includes a second absorbent pad between said grid and said reservoir chamber and a second porous membrane between said second absorbent pad and said reservoir chamber.

10. A nasal clip as set forth in claim 9 wherein each said bulbous portion includes a wick disposed in and extending through said reservoir chamber to said second porous membrane for conveying the medicant from said reservoir chamber to said second porous membrane.

11. A nasal clip as set forth in claim 5 wherein said medicant volatilizes at a temperature of 98.6° F.

12. A medical device for insertion in a nose of a user comprising
a nasal cannula having a pair of tubes configured for positioning in and delivering oxygen to a pair of nasal passages of the nose of a user; and
a nasal clip mounted between said tubes of said nasal cannula, said nasal clip including a pair of limbs extending towards each other and configured for positioning in the nasal passages of the nose of the user, a gusset connecting said pair of limbs together at a base thereof and integrally attached to said cannula and a pair of bulbous portions, each said bulbous portion being disposed on an end of a respective limb and configured for insertion into the nose of a user for delivery of a medicant thereto.

13. A medical device as set forth in claim 12 wherein said pair of bulbous portions are biased into contact with each other and configured for engagement with septum mucosa in the nose of a user.

14. A medical device as set forth in claim 13 wherein said nasal clip is made of a heat sensitive plastic having at least one of a volatile medicant and a volatile therapeutic aromatic material infused therein and configured for delivery to the nose of the user.

15. A medical device as set forth in claim 13 wherein each said bulbous portion includes a reservoir chamber for receiving at least one medicant of a, a grid disposed over said chamber to deliver the medicant from said chamber and a porous membrane disposed over said grid to diffuse the medicant therefrom.

16. A medical device as set forth in claim 12 wherein said nasal clip contains a medicant in the form of a volatile material.

17. A medical device as set forth in claim 12 wherein said nasal clip contains a medicant in the form of a therapeutic aromatic material.

18. A medical device as set forth in claim 2 further comprising a nasal cannula Integral with said gusset rib and having a pair of tubes configured for positioning in and delivering oxygen to a pair of nasal passages of the nose of a user.

* * * * *

UNITED STATES PATENT AND TRADEMARK OFFICE
CERTIFICATE OF CORRECTION

PATENT NO. : 10,406,338 B2
APPLICATION NO. : 15/183345
DATED : September 10, 2019
INVENTOR(S) : Richard A. Davi It is certified that error appears in the above-identified patent and that said Letters Patent is hereby corrected as shown below:

In the Claims

Column 12, Line 45, cancel "of a".

Signed and Sealed this
Twenty-ninth Day of October, 2019

Andrei Iancu
*Director of the United States Patent and Trademark Office*